United States Patent [19]

Rutherford et al.

[11] Patent Number: 5,376,636

[45] Date of Patent: * Dec. 27, 1994

[54] METHOD FOR PROMOTING TISSUE REPAIR AND REGENERATION USING PDGF AND GLUCOCORTICOIDS

[75] Inventors: Robert B. Rutherford, Farmington, Conn.; Marc F. Charette, Needham, Mass.

[73] Assignees: Creative BioMolecules, Inc., Hopkinton, Mass.; The University of Conn., Storrs, Conn.

[ * ] Notice: The portion of the term of this patent subsequent to Sep. 22, 2007 has been disclaimed.

[21] Appl. No.: 849,931

[22] Filed: Mar. 12, 1992

Related U.S. Application Data

[63] Continuation-in-part of Ser. No. 669,070, Mar. 12, 1991, Pat. No. 5,149,691.

[51] Int. Cl.$^5$ .............................................. A61K 37/36
[52] U.S. Cl. ........................................... 514/12; 514/2; 514/8; 514/21
[58] Field of Search ........................ 514/2, 8, 12, 21

[56] References Cited

U.S. PATENT DOCUMENTS

| | | | |
|---|---|---|---|
| 4,808,402 | 2/1989 | Leibovich et al. | 424/423 |
| 4,861,757 | 8/1989 | Antoniades et al. | 514/21 |
| 4,874,746 | 10/1989 | Antoniades et al. | 514/21 |
| 5,124,316 | 6/1992 | Antoniades et al. | 514/2 |
| 5,149,691 | 9/1992 | Rutherford | 514/12 |

OTHER PUBLICATIONS

Levenson et al. (1985), Journal of Biol. Chem. pp. 8056–8063.
Cheung et al. (1978), Proc. of Soc. Exp. Bio. & Med., vol. 158(2), pp. 292–297.
Merck Index, 1983, pp. 2510, 2909, 4689, 4690.
Arch—Oral. Biol.—vol. 37(2) pp. 139–145 (1992) Rutherford et al.
J. Clin. Periodontol—vol. 20, pp. 537–544 (1993), Rutherford et al.

*Primary Examiner*—Howard E. Schain
*Attorney, Agent, or Firm*—Testa, Hurwitz & Thibeault

[57] ABSTRACT

Disclosed is a method for the regeneration of tissue, the treatment of external wounds and the treatment of periodontal disease comprising applying to the affected tissue an effective amount of a composition comprised of platelet-derived growth factor (PDGF) and an anti-inflammatory compound. The presence of the anti-inflammatory compound potentiates the activity of PDGF in stimulating cell growth, thereby enhancing tissue regeneration and/or wound healing.

12 Claims, 6 Drawing Sheets

METHOD FOR PROMOTING TISSUE REPAIR AND REGENERATION USING PDGF AND GLUCOCORTICOIDS

This application is a continuation-in-part of Ser. No. 07/669,070, filed Mar. 12, 1991 and now U.S. Pat. No. 5,149,691.

BACKGROUND OF THE INVENTION

Polypeptide growth factors are a class of natural biological mediators that regulate the proliferation, differentiation, motility and matrix synthesis of nearly all cell types. These properties, demonstrable in vivo, have led to the proposal that such factors play important roles in soft and hard tissue repair. Platelet-derived growth factor (PDGF) is a well characterized example of such a polypeptide growth factor.

PDGF is a peptide hormone produced by blood platelets which influences the regulation of a broad array of biological systems including wound repair, arteriosclerosis, neoplasia, embryogenesis and bone marrow fibrosis. PDGF is a mitogen, that is, a substance which induces mitosis of cells and thus cellular proliferation. In wound repair, PDGF elicits both chemotactic and mitogenic responses in fibroblasts, smooth muscle, glial cells, etc. Injury to the endothelium lining the vessel wall is believed to cause platelets to adhere to exposed connective tissue at the wound site, with the concomitant release of PDGF. The released PDGF is thought to chemotactically recruit many cell types including fibroblasts, monocytes, glial and smooth muscle to migrate into the site of the wound. Increased proliferation of these cells leads to accelerated tissue regeneration and wound healing.

It has been demonstrated that the mitogenic properties of PDGF can be augmented by the addition of growth factors. For example, Antonaides et al. in U.S. Pat. Nos. 4,861,757 and 4,874,746 showed that a combination of PDGF and insulin-like growth factor-1 (IGF-1) or transforming growth factor alpha (TGF-$\alpha$) had a greater effect on cell mitogenic activity than PDGF alone.

The effect of combining PDGF with other compounds is less clear. Levenson et al. in *J. Biol. Chem.*,260:8056–63 (1985), showed that the synthetic glucocorticoid, dexamethasone, acts synergistically with cartilage-derived growth factor (CDGF) to enhance the stimulation of DNA synthesis in quiescent Swiss 3T3 cells, while having only a neutral effect with PDGF. In addition, Levenson et al. showed that the addition of dexamethasone to PDGF-stimulated cultures had no effect on DNA synthesis over that observed with PDGF alone.

SUMMARY OF THE INVENTION

The present invention relates to a method for enhancing tissue regeneration and/or wound repair in a mammal comprising applying to the tissue or wound an effective amount of a composition comprising an anti-inflammatory compound and PDGF. The method promotes cellular activity at the site of the wound which expedites healing of the wound.

More specifically, the combination of PDGF and anti-inflammatory compound synergistically promotes the proliferation of mammalian cells at the site. Either natural-sourced or recombinant PDGF can be used in the composition. It has been found that many anti-inflammatory agents can synergistically enhance the mitogenic effect of PDGF on cells. Anti-inflammatory agents which are particularly useful are a class of compounds known as glucocorticoids. Glucocorticoids include cortisone, hydrocortisone (cortisol), dexamethasone, and pharmacologically active derivatives thereof, for example.

The method of the present invention can be used to promote tissue regeneration and/or wound healing in a variety of tissues. The method is effective for enhancing tissue regeneration and wound healing in epithelial tissues, and for promoting regeneration of bone and/or cartilage tissues. In general, applying the composition to an area where epithelium, bone or cartilage has been broken, torn or eroded due to injury or disease, for example, stimulates the regeneration and repair of the epithelium, bone or cartilage.

The method is particularly effective for treating tissues affected by periodontal disease. The method is carried out by applying a composition of PDGF and the anti-inflammatory compound to the affected gum tissue and periodontal ligament. The composition promotes. regeneration of the gum tissue, of tooth tissues such as dentin and pulp, and of the connective tissue holding the tooth in place in the gum.

The present method provides an effective therapeutic composition for treating external wounds, including skin ulcers, burns and lesions and for regenerating connective tissue and/or bone. The method is particularly effective for treating dental tissue affected by periodontal disease.

DETAILED DESCRIPTION OF THE INVENTION

Figure 1:
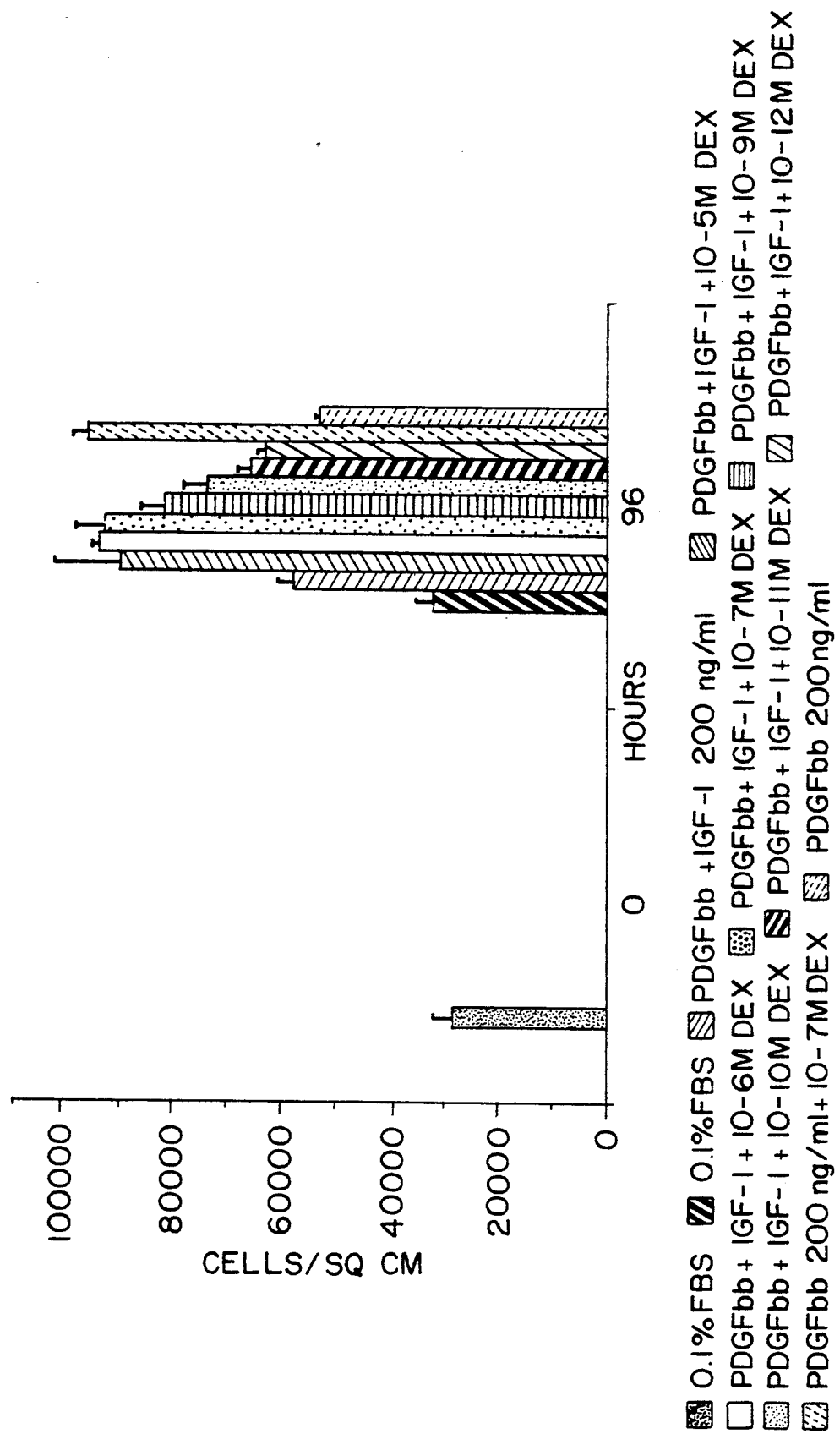
FIG. 1 is a graph showing the influence of dexamethasone on the mitogenic activity of both PDGF alone and PDGF+IGF-1.

The present method comprises applying a combination of PDGF and an anti-inflammatory compound to a tissue.

Native PDGF is a dimeric molecule comprised of two polypeptide chains, one or more of which may be glycosylated. The two chains (referred to as alpha ($\alpha$), and beta ($\beta$)) are homologous but not identical. The $\alpha$ chain has a molecular weight of about 17,000 to 18,000 and the $\beta$ chain has a molecular weight of about 13,000 to 14,000. The $\alpha$ and $\beta$ chains are synthesized in vivo from larger molecules which are subsequently processed at the amino and carboxyltermini. The mature human $\alpha$ chain is comprised of 110 or 125 amino acids and various N-linked sugar side chains, and the length and amino acid sequence is dependent on the tissue source. The fully processed human $\beta$ chain is encoded by the c-sis gene and is comprised of 112 amino acids. Biologically active PDGF can exist as a homodimer e.g., $\alpha\alpha$, $\beta\beta$, or a heterodiminer $\alpha\beta$. The molecular weights of the $\alpha\alpha$ homodimer and $\beta\beta$ homodimer are about 35,000 and about 32,000, respectively.

PDGF useful in the present invention may be natural sourced, recombinant or synthetic PDGF. Natural sourced PDGF can be extracted from human platelets, for example as described by Heidin et al. (1979) *Proc. Natl. Acad. Sci. USA*, 76:3722-33726; Antoniades et al. (1979) *Proc. Natl. Acad. Sci. USA*, 76:1809-1813; Antoniades et al., U.S. Pat. No. 4,479,896; and Lipton et al., U.S. Pat. No. 4,350,687. Recombinant PDGF can be produced using transformed eucaryotic cells, such as yeast, (See, EP Publication No. 0177957), or procaryotic cells such as *E. coli*. PDGF also can be synthesized using art-recognized peptide synthesis techniques. Biologically active fragments, derivatives or mutant forms of PDGF can be used in the present invention. PDGF which can be used is commercially available, for example, from Amgen Corporation, Thousand Oaks, Calif.; PDGF Inc., Boston, Mass.; Collaborative Research Inc., Waltham, Mass.; and Creative BioMolecules, Inc., Hopkinton, Mass.

Anti-inflammatory compounds are compounds which reduce inflammation by acting on body mechanics without directly antagonizing the causative agent. A class of anti-inflammatory compounds which is particularly useful in the present method comprises glucocorticoids. Glucocorticoids include, for example, cortisone, hydrocortisone (cortisol), dexamethasone and pharmacologically active derivatives of these drugs, e.g., hydrocortisone acetate. Dexamethasone and cortisol are commercially available from a number of sources, for example, Sigma Chemical Co., Saint Louis, Mo.

Wound healing and tissue regeneration can be promoted by directly, locally applying an effective amount of a composition comprising PDGF and the selected anti-inflammatory compound to the affected tissue. The tissue can be external epithelial tissue, internal epithelial tissue, bone, cartilage, or dental tissue, including gum tissue, dentin, pulp, cementum or periodontal ligature.

The concentration of PDGF and of the anti-inflammatory compound will depend in part upon the compound selected, its potency and the tissue it is applied to. The amount can be determined empirically by applying a low dose and observing the effects and incrementally increasing the dose until the desired effect is obtained. A concentration of PDGF of from about 0 $\mu$g/ml to about 10 mg/ml is effective for most applications. For many glucocorticoids, a concentration of from about $10^{-5}$ M to about $10^{-12}$ M can be used. For example, a concentration of from about $10^{-5}$ M to about $10^{-12}$ M of dexamethasone has been shown to significantly enhance the activity to PDGF. A composition containing from about 3.92 $\mu$g/ml ($10^{-5}$ M) to about 0.000392 mg/ml ($10^{-12}$ M of dexamethasone (which has a molecular weight of about 392 $\mu$g/mole) is preferred for most applications. A concentration of about $10^{-5}$ to about $10^{-9}$M is most preferred.

Other growth factors such as transforming growth factor-$\alpha$ (TGF-$\alpha$) and insulin-like growth factors (IGF-1) can be added to the composition containing PDGF and the anti-inflammatory compound to further enhance healing or regeneration of injured tissue. TGF-$\alpha$, IGF-1 or other growth factor can be added to the PDGF mixture in a weight-to-weight ratio (of PDGF to growth factor), for example, of between about 1:4 and 25:1, preferably between about 1:2 and 10:1, and more preferably 1:1 or 2:1.

In a preferred embodiment of the present invention, the composition of PDGF and the anti-inflammatory compound is combined with a pharmaceutically acceptable carrier substance for local, topical administration. Examples of pharmaceutically acceptable carriers include, for example, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example, anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

The amounts of PDGF and anti-inflammatory compound incorporated into the formulation of the present invention is not critical; the concentration should be sufficient to permit ready application of the formulation to the wound area in an amount which will deliver the desired amount of PDGF and the anti-inflammatory compound. A typical gel formulation useful for the topical administration of PDGF and dexamethasone, for example, comprises the following:

|  | % by Weight |
| --- | --- |
| sterile distilled water | 92.38 |
| sodium dibasic phosphate | 0.03 |
| Carbapol TM | 0.5 |
| glycerin | 1.6 |
| m-cresol | 0.25 |
| sodium hydroxide (1N) | 0.5 |

A bone collagen matrix as described in U.S. Pat. No. 4,975,526, which is incorporated herein by reference, can be used as the carrier for application to bone and/or cartilage. The collagen matrix described in this patent is a biodegradable, biocompatible, mineral-free, insoluble Type-I bone collagen particles being depleted of non-collagenous protein. The collagen matrix particles have a mean diameter of about 70 $\mu$m-850 $\mu$m, and an increased intraparticle surface area relative to untreated material. In this embodiment, PDGF and the anti-inflammatory agent are first dissolved in a suitable solvent such as buffered sterile saline and then added to the collagen matrix. The mixture is vortexed, and the matrix is lyophilized and shaped as desired or implanted into an area of bone or cartilage by packing.

Other useful matrix materials include synthetic homopolymers and copolymers of glycolic acid and lactic acid, hydroxyapatite, tricalcium and other calcium phosphates, and particulate demineralized guanidine extracted species-specific (allogenic) bone. The matrix containing the PDGF and steroid can be applied into a shape spanning the bone or cartilage defect to serve as a "temporary scaffold" and substratum as a base for anchoring and proliferation of differentiated tissue cells.

The method is particularly useful for treating tissues affected by periodontal disease. Periodontal disease is characterized by gingivitis, destruction of alveolar bone and periodontal ligament, apical migration of the epithelial attachment resulting-in the formation of periodontal pockets. Thus, a number of different tissues are involved, including epithelium, cartilage and bone. The method of the invention promotes healing and regeneration of the gum tissues (epithial tissue) the periodontal ligament (cartilage) and the jaw bone (bone). Pulp and dentin tissue within the tooth which was eroded or attacked by periodontal disease can be regenerated using the present method. The most preferred composition for this purpose is a combination of PDGF and dexamethasone.

The data shown in the following Examples all demonstrate that PDGF mitogenesis is enhanced in the presence of a glucocorticoid. Current methodologies described in the literature disclose the use of PDGF as an agent to enhance tissue repair or reduce regeneration in vivo utilizing another human growth factor, IGF-1 in combination with PDGF. This is substantially more expensive and less effective than using the small amounts (e.g., less than $10^{-5}$M) of glucocorticoid drugs, as described herein. In addition, the glucocorticoids have anti-inflammatory properties, which are beneficial where inflammation is present, such as with many periodontal diseases. As demonstrated herein, the addition of a glucocorticoid drug in a preferred concentration of from about $10^{-7}$M to about $10^{-9}$M was consistently more effective than adding 1 μg/ml IFG-1 for enhancing the cell proliferation which is the basis of tissue regeneration and repair.

The invention will be more readily understood by the following specific non-limiting examples which are included for purposes of illustration.

EXAMPLES

Example 1:

Potentiation of mitogenic effect of PDGF and IGF-1 by Dexamethasone

The following experiments were all performed on low passage, human diploid fibroblasts obtained from the periodontal ligaments and dental pulps of extracted teeth. The cells were cultured under standard culture conditions and stocks were propagated with 10% fetal bovine serum (FBS) as the source of growth factors. For the experiments detailed here, the cells were plated at 10,000 to 15,000 cells per 1.88 cm² of surface area in 24 well culture plates and conditioned in medium containing 0.1% FBS for 24–48 hours prior to treatment. The cells were then exposed once to the indicated concentrations of PDGF, IGF-1 and/or dexamethasone in culture media at time zero. The cells were quantitatively harvested from each well and the total cell population densities were determined using a Coulter counter by standard methods. The PDGF-$\beta\beta$ and PDGF-$\alpha\alpha$ used in these studies were recombinant human analogs of PDGF produced in *E. coli* which were provided by Creative BioMolecules, Hopkinton, Mass. The dexamethasone was purchased from Sigma Chemical Company, St. Louis, Mo.

Cell cultures in 24 well plates prepared as described above were treated with the following materials and the extent of cell growth determined.

Plate 1 contained 0.1% FBS
Plate 2 contained 0.1% FBS
Plate 3 contained PDGF-$\beta\beta$ 200 ng/ml + 1GF-1 200 ng/ml
Plate 4 contained PDGF-$\beta\beta$ 200 ng/ml + 1GF-1 200 ng/ml + $10^{-5}$M Dexamethasone
Plate 5 contained PDGF-$\beta\beta$ 200 ng/ml + 1GF-1 200 ng/ml + $10^{-6}$M Dexamethasone
Plate 6 contained PDGF-$\beta\beta$ 200 ng/ml + 1GF-1 200 ng/ml + $10^{-7}$M Dexamethasone
Plate 7 contained PDGF-$\beta\beta$ 200 ng/ml + 1GF-1 200 ng/ml + $10^{-9}$M Dexamethasone
Plate 8 contained PDGF-$\beta\beta$ 200 ng/ml + 1GF-1 200 ng/ml + $10^{-10}$M Dexamethasone
Plate 9 contained PDGF-$\beta\beta$ 200 ng/ml + 1GF-1 200 ng/ml + $10^{-11}$M Dexamethasone
Plate 10 contained PDGF-$\beta\beta$ 200 ng/ml + 1GF-1 200 ng/ml + $10^{-12}$M Dexamethasone
Plate 11 contained PDGF-$\beta\beta$ 200 ng/ml + $10^{-7}$M Dexamethasone
Plate 12 contained PDGF-$\beta\beta$ 200 ng/ml.

All of the plates except for plate 1 were incubated for 96 hours. Plate 1 was incubated for 30 minutes. The cells then were removed from the plates and counted. The efficacy of the agents on cell mitogenic activity was measured by the number of cells per square centimeter after the incubation period.

Figure 2:
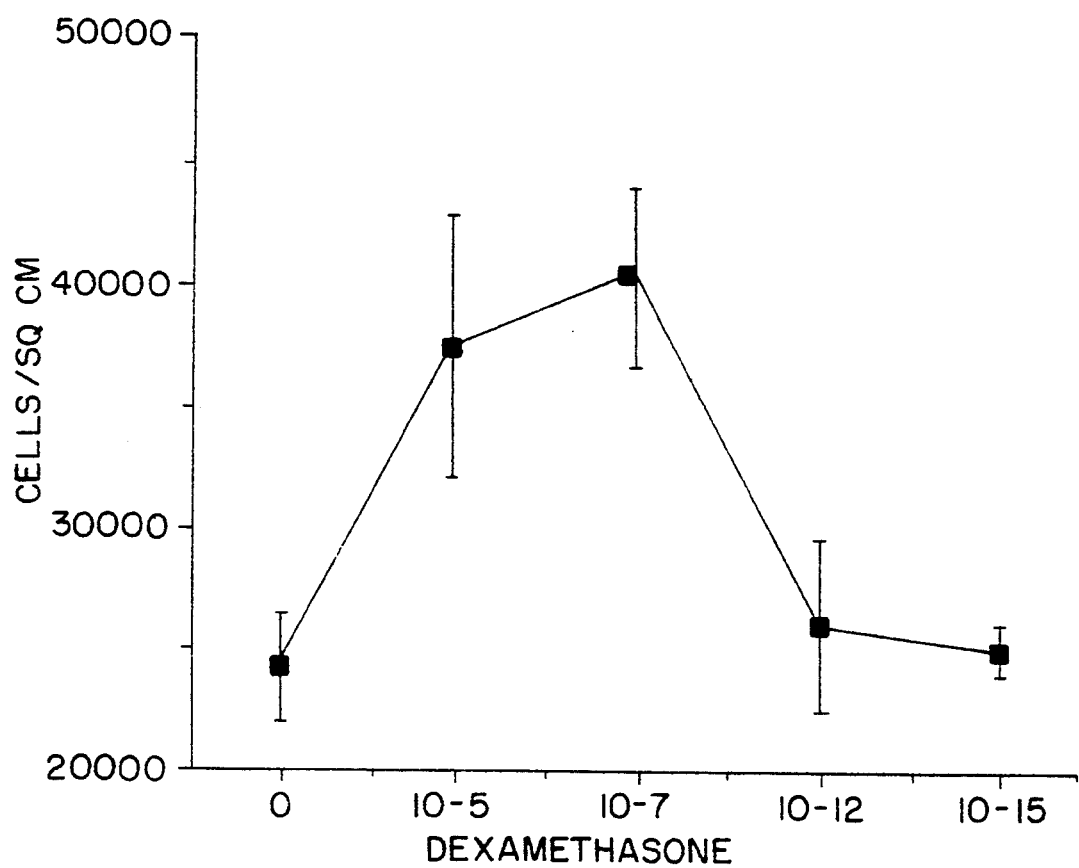
FIG. 2 is a graph showing the effect on cell population density of various concentrations of dexamethasone and PDGF+IGF-1.
Figure 4A:
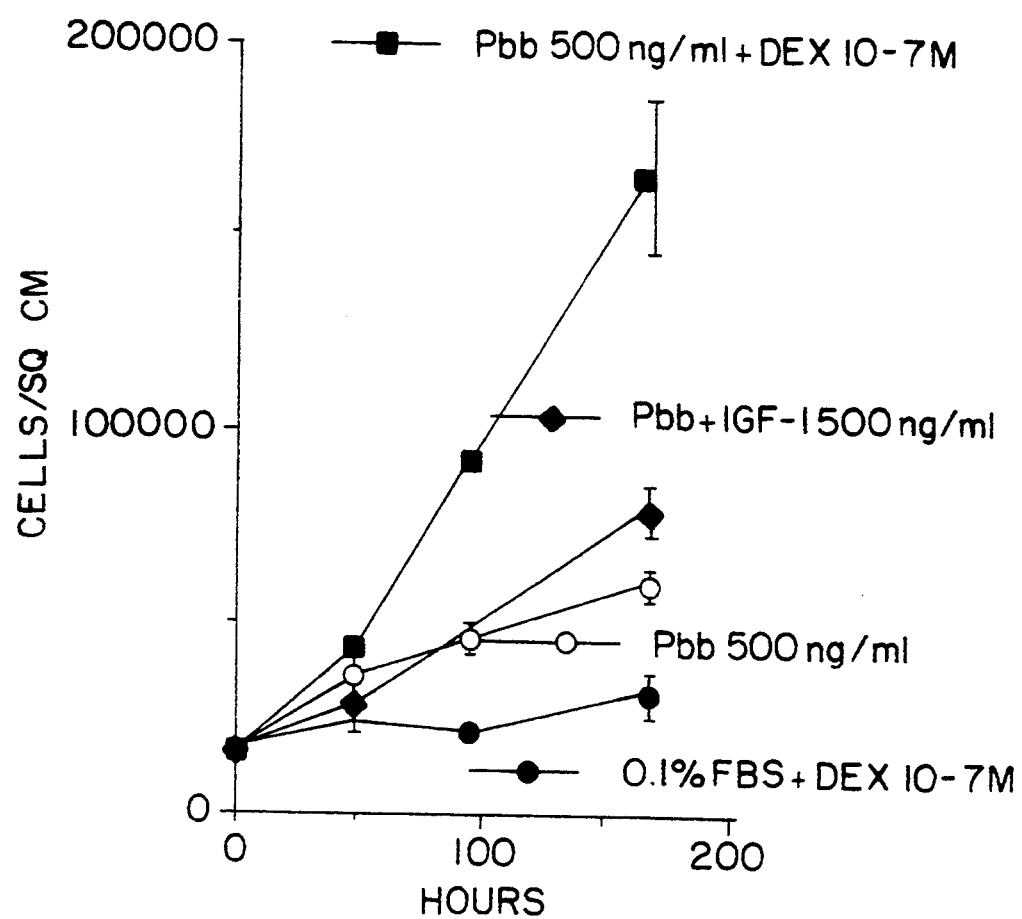
FIGS. 4A and 4B are a graph comparing the mitogenic activity of PDGF-$\alpha\alpha$ and PDGF-$\beta\beta$.
Figure 4B:
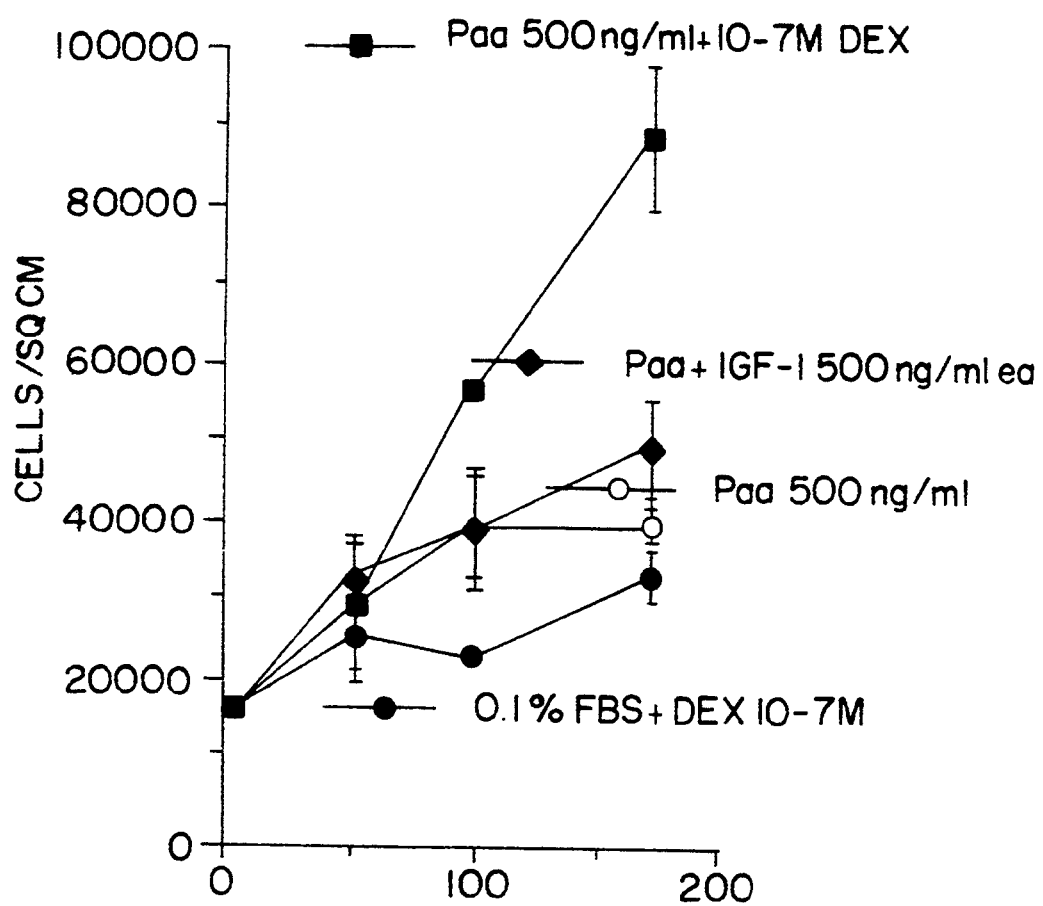

The results are illustrated in FIGS. 1-2. FIG. 1 shows that cultures treated with dexamethasone in combination with PDGF proliferated faster than cultures treated with PDGF alone and PDGF+IGF-1. FIG. 2 shows that dexamethasone is effective in enhancing all proliferation over concentrations ranging from $10^{-5}$ to $10^{-11}$M. The concentration of dexamethasone to optimally potentiate the mitogenic activity of PDGF at 200 ng/ml is about $10^{-7}$M. The mitogenic activity of the cells was increased by the combination of dexamethasone and PDGF more than by just PDGF alone or PDGF+IGF-1. However, there was no further enhancement of mitogenic activities by the addition of IGF-1 to PDGF and dexamethasone. Dexamethasone alone has no effect on cell mitogenic activity, as shown in FIG. 4.

Example 2

Comparison of the effects on mitogenic activity of dexamethasone with IGF-1 over time.

To determine the time course of the effects of dexamethasone on PDGF-$\beta\beta$ mitogenic activity, cultures were treated with PDGF+IGF-1 and PDGF with and without dexamethasone at $10^{-7}$ and $10^{-12}$M, harvested and counted at the time indicated over a period of 160 hours. Data from the same experiment are plotted against the controls in two separate plots for clarity.

Figure 3A:
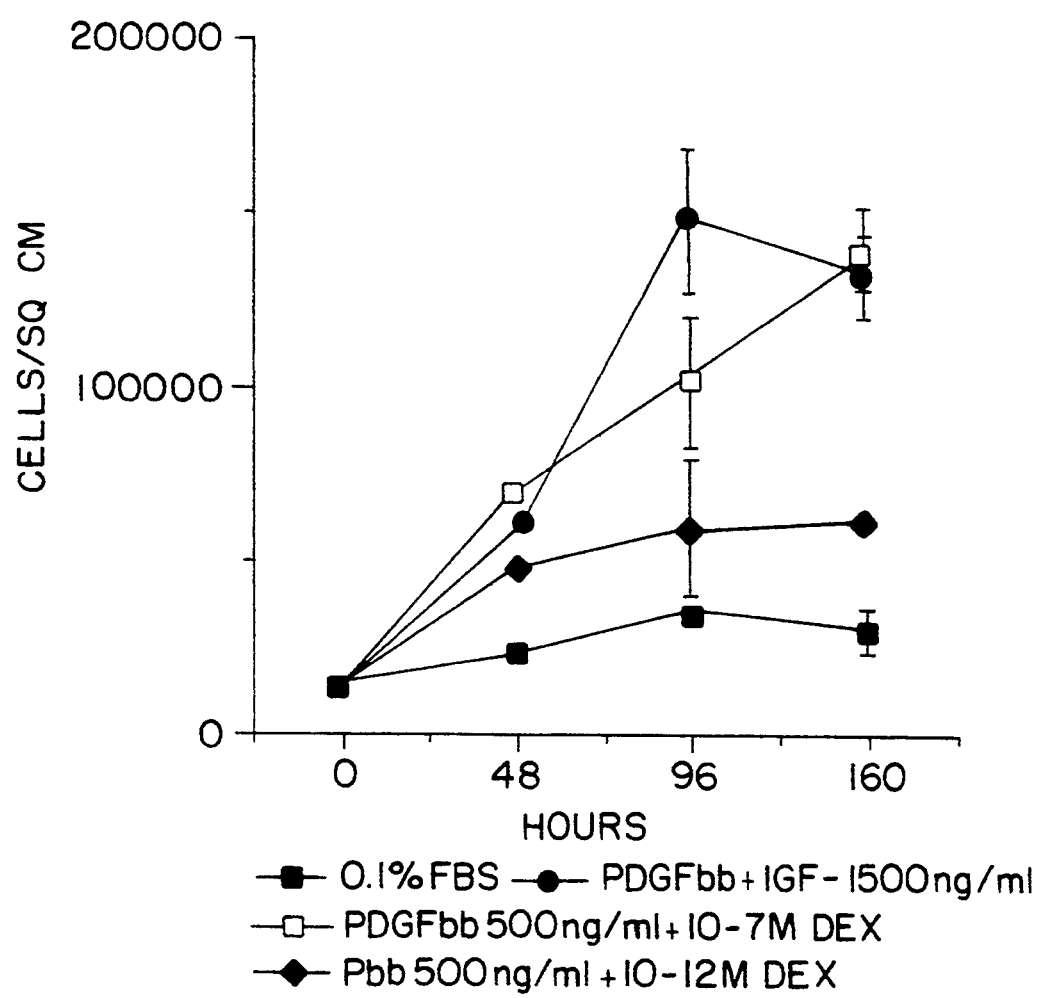
FIGS. 3A and 3B are a graph showing the influence of dexamethasone on the mitogenic activity of PDGF using PDGF+IGF-1 as a control reference.
Figure 3B:
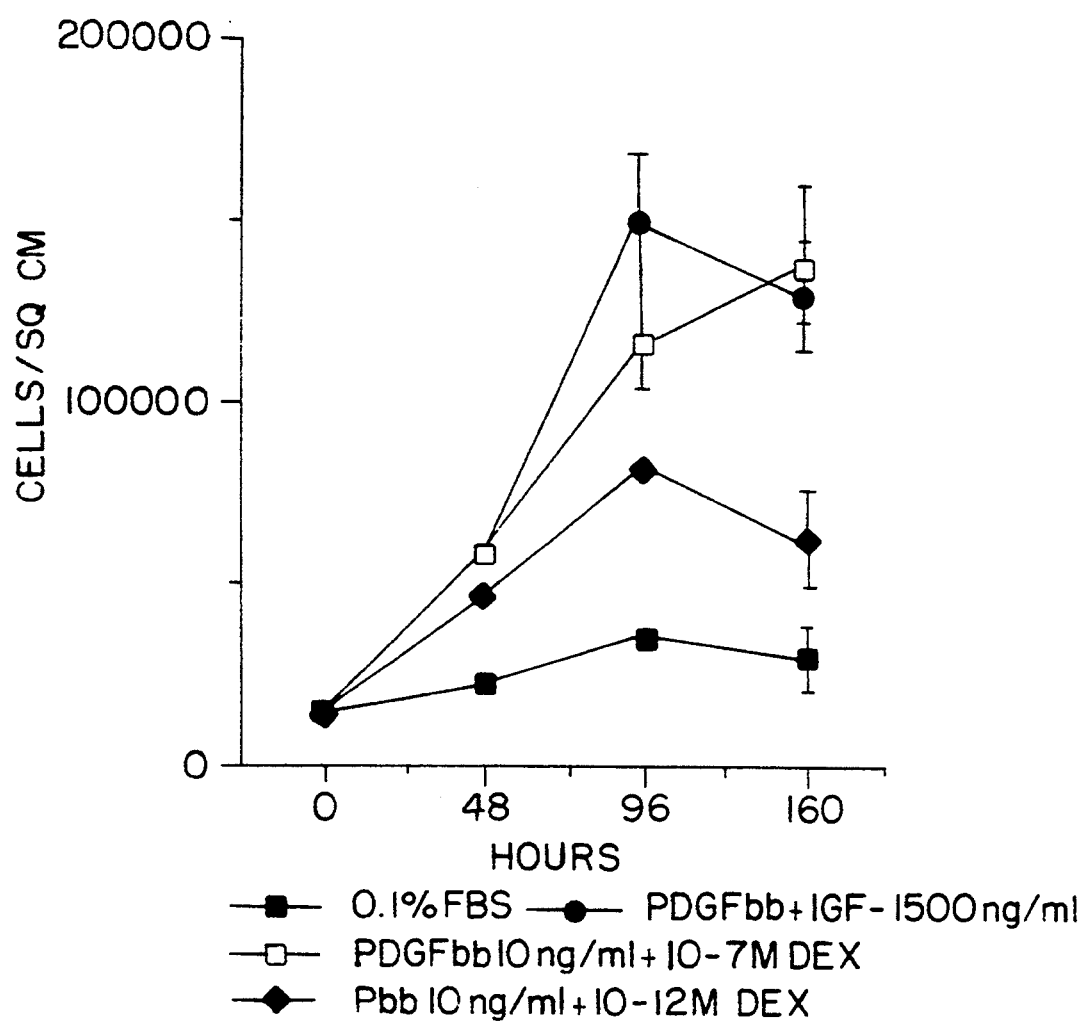

The results, shown in FIG. 3, revealed that a single exposure of the cultured cells at time zero to PDGF-$\beta\beta$ plus dexamethasone resulted in final increased cell population densities after 160 hours that were similar to those obtained by exposure of the cultured cells to PDGF-$\beta\beta$ plus IGF-1. The final total cell number was similar for treatment with 10 ng/ml and 500 ng/ml PDGF-$\beta\beta$. The PDGF-$\beta\beta$+IGF-1 treated cultures reached maximal cell population densities at 96 hours, while those exposed to PDGF-$\beta\beta$+dexamethasone had not plateaued by 160 hours, demonstrating the prolonged effect of a single dose of PDGF+dexamethasone on cell proliferation.

Example 3

Comparison of the Mitogenic Activity of PDGF-$\alpha\alpha$ and PDGF-$\beta\beta$.

Plates prepared as described above were treated with PDGF-$\alpha\alpha$ or PDGF-$\beta\beta$ and dexamethasone or IGF-1. The extent of cell growth determined.

PDGF-$\beta\beta$ Studies

Plate 1 contained 0.1% FBS+$10^{-7}$M dexamethasone.

Plate 2 contained PDGF-$\beta\beta$ 500 ng/ml.

Plate 3 contained PDGF-$\beta\beta$ 500 ng/ml+IGF-1 500 ng/ml.

Plate 4 contained PDGF-$\beta\beta$ 500 ng/ml+$10^{-5}$M dexamethasone.

PDGF-$\alpha\alpha$ Studies

Plate 5 contained 0.1% FBS_$10^{-7}$ dexamethasone.

Plate 6 contained PDGF-$\alpha\alpha$ 500 ng/ml.

Plate 7 contained PDGF-$\alpha\alpha$ 500 ng/ml+IGF-1 500 ng/ml.

Plate 8 contained PDGF-$\alpha\alpha$ 500 ng/ml+$10^{-7}$M dexamethasone.

The results of the present experiment, shown in FIG. 4, which demonstrate that dexamethasone potentiates the mitogenic activity of both PDGF-$\alpha\alpha$ and PDGF-$\beta\beta$. As shown in FIG. 4, after a single application of PDGF plus dexamethasone, the rate of cell proliferation at 168 hours did not appear to have diminished. The data shown in Table 1 suggest that PDGF-$\beta\beta$ is a more potent mitogen for these cells than PDGF-$\alpha\alpha$, and that PDGF-$\beta\beta$ treated cultures may be slightly more responsive to dexamethasone than PDGF-$\alpha\alpha$ treated cultures.

TABLE 1

| | Ratios of Cell Population Densities | |
|---|---|---|
| PDGF-$\beta\beta$ DEX/PDGF-$\beta\beta$ | PDGF-$\alpha\alpha$ DEX + PDGF-$\alpha\alpha$ | PDGF-$\beta\beta$ + PDGF-$\alpha\alpha$ |
| 48 HOURS 1.24 | 0.92 | 1.08 |
| 96 HOURS 1.97 | 1.44 | 1.32 |
| 168 HOURS 2.73 | 2.19 | 1.57 |

Data are ratios of means of cells/cm$^2$ from replicate experiments.

Equivalents

One skilled in the art will be able to ascertain, with no more than routine experimentation, many equivalents to the specific embodiments described herein. Such equivalents are intended to be encompassed by the following claims.

We claim:

1. A method for promoting regeneration or repair of a tissue in a mammal comprising:
    applying to the tissue a regenerating amount of a composition comprising PDGF in a concentration of from about 0.1 $\mu$g/ml to about 10 mg/ml and a glucocorticoid in a concentration of from about $10^{-5}$M to about $10^{-12}$M.

2. A method of regenerating or repairing dental tissue in a mammal comprising the steps of:
    applying to said dental tissue a regenerating amount of a composition comprising PDGF in a concentration of from about 0.1 $\mu$g/ml to about 10 mg/ml and a glucocorticoid in a concentration of from about $10^{-5}$M to about $10^{-12}$M.

3. The method of claims 1 or 2 wherein the tissue comprises epithelium.

4. The method of claims 1 or 2 wherein the tissue comprises bone or cartilage.

5. The method of claims 1 or 2 wherein the composition further comprises a pharmaceutically acceptable carrier.

6. The method of claims 1 or 2 wherein the glucocorticoid is selected from the group consisting of dexamethasone, cortisone and hydrocortisone.

7. A composition for promoting regeneration or repair of a tissue in a mammal comprising PDGF in a concentration of 0.1 $\mu$g/ml to 10 mg/ml and a glucocorticoid compound in a concentration of $10^{-5}$M to about $10^{-12}$M.

8. A composition for regenerating or repairing dental tissue in a mammal comprising PDGF in a concentration of 0.1 $\mu$g/ml to 10 mg/ml and a glucocorticoid compound in a concentration of $10^{-5}$M to about $10^{-12}$M.

9. The composition of claim 7 or 8 wherein the glucocorticoid is selected from the group consisting of dexamethasone, cortisone and hydrocortisone.

10. The composition of claims 7 or 8 further comprising a growth factor in a growth factor:PDGF ratio of from about 1:4 to about 25:1.

11. The composition of claim 10 wherein the growth factor is selected from the group consisting of transforming growth factor-$\alpha$ and insulin-like growth factors.

12. The composition of claims 7 or 8 wherein the composition further comprises a pharmaceutically acceptable carrier.

* * * * *